(12) United States Patent
Kinoshita et al.

(10) Patent No.: US 10,758,685 B2
(45) Date of Patent: Sep. 1, 2020

(54) ULTRASONIC NEBULIZER

(71) Applicant: OMRON HEALTHCARE CO., LTD., Muko-shi, Kyoto (JP)

(72) Inventors: Shigeo Kinoshita, Kyoto (JP); Takaaki Okanishi, Kyoto (JP); Makoto Tabata, Kyoto (JP); Hiroshi Ogawa, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 497 days.

(21) Appl. No.: 15/698,438

(22) Filed: Sep. 7, 2017

(65) Prior Publication Data

US 2017/0368270 A1 Dec. 28, 2017

Related U.S. Application Data

(63) Continuation of application No. PCT/JP2016/050866, filed on Jan. 13, 2016.

(30) Foreign Application Priority Data

Mar. 25, 2015 (JP) ................................. 2015-063267

(51) Int. Cl.
*A61M 11/00* (2006.01)
*B05B 12/08* (2006.01)
(Continued)

(52) U.S. Cl.
CPC ........... *A61M 11/005* (2013.01); *A61M 11/00* (2013.01); *B05B 12/081* (2013.01);
(Continued)

(58) Field of Classification Search
CPC ................ A61M 11/00; A61M 11/005; A61M 11/0085; A61M 16/14; A61M 16/16;
(Continued)

(56) References Cited

U.S. PATENT DOCUMENTS 6,152,383 A * 11/2000 Chen .................... B05B 17/0615
128/200.16
2009/0261185 A1* 10/2009 Kasuya ................... B05B 17/04
239/690
(Continued)

FOREIGN PATENT DOCUMENTS

CN 102355915 A 2/2012
JP H04-099255 U 8/1992
(Continued)

OTHER PUBLICATIONS

Apr. 5, 2016 International Search Report issued in International Patent Application No. PCT/JP2016/050866.
(Continued)

*Primary Examiner* — Samchuan C Yao
*Assistant Examiner* — Margaret M Luarca
(74) *Attorney, Agent, or Firm* — Oliff PLC

(57) ABSTRACT

An ultrasonic nebulizer includes a working tank configured to be detachable with respect to a main body. The working tank includes a rod-shaped tank-side contact electrode that extends in a vertical direction along an outer wall of the working tank. A specific portion that corresponds to a portion in a circumferential direction of the outer circumferential surface of the tank-side contact electrode is exposed from the outer wall, and the remaining portion of the outer circumferential surface of the tank-side contact electrode is embedded inside of the outer wall and is connected to an electrode of an ultrasonic vibrator. A main body-side contact electrode comes into contact with the specific portion of the outer circumferential surface of the tank-side contact electrode when the working tank is mounted on the main body.

8 Claims, 10 Drawing Sheets

(51) Int. Cl.
*B05B 17/06* (2006.01)
*G01F 23/296* (2006.01)

(52) U.S. Cl.
CPC ...... *B05B 17/0607* (2013.01); *G01F 23/2962* (2013.01); *A61M 2205/18* (2013.01); *A61M 2205/3375* (2013.01); *A61M 2205/3389* (2013.01); *A61M 2205/502* (2013.01)

(58) Field of Classification Search
CPC . B05B 17/06; B05B 17/0615; B05B 17/0607; F24F 6/008
See application file for complete search history.

(56) References Cited

U.S. PATENT DOCUMENTS

2011/0290241 A1* 12/2011 Maeda ................ A61M 11/005
128/200.14

2015/0208524 A1* 7/2015 Kontani ............... H05K 7/1432
361/752

FOREIGN PATENT DOCUMENTS

| JP | H05-137786 A | 6/1993 |
|----|--------------|--------|
| JP | H05-070668 A | 9/1993 |
| JP | 2004-121605 A | 4/2004 |
| JP | 2005-278742 A | 10/2005 |
| JP | 2006-217955 A | 8/2006 |
| WO | 2010/106834 A1 | 9/2010 |

OTHER PUBLICATIONS

Sep. 10, 2019 Office Action issued in Chinese Patent Application No. 201680010811.7.

* cited by examiner

ULTRASONIC NEBULIZER

TECHNICAL FIELD

The present invention relates to an ultrasonic nebulizer, and more specifically, relates to an ultrasonic nebulizer that transmits ultrasonic vibration generated by an ultrasonic vibrator to a medicine tank via a working liquid in a working tank and thereby atomizes a medicinal liquid in the medicine tank.

BACKGROUND ART

Conventionally, as this type of ultrasonic nebulizer, there is known to be an ultrasonic nebulizer that includes an atomizer that is configured to be detachable with respect to a main body, as disclosed in Patent Document 1 (JP 2005-278742A), for example. A power converter that converts AC power from a power source cord, a control circuit that outputs a control signal, and the like are installed in the main body, and an external connection terminal (contact electrode) that is to be connected to the atomizer is provided on the main body. The atomizer contains a storage portion that stores liquid to be atomized (medicinal liquid), a storage portion that stores a transmission liquid (working liquid), an ultrasonic wave generator, and a power source unit. If the atomizer is mounted on the main body, the outputs of the power converter and the control circuit in the main body are supplied to the power source unit of the mounted atomizer via the external connection terminal. During use, in the atomizer, the ultrasonic waves from the ultrasonic wave generator are transmitted to the liquid to be atomized via the transmission liquid, and the liquid to be atomized is atomized.

CITATION LIST

Patent Literature

Patent Document 1: JP 2005-278742A

SUMMARY OF INVENTION

Technical Problem

Incidentally, from a hygienic viewpoint such as preventing the risk of infection, it is preferable that a working tank storing a working liquid is periodically washed and/or disinfected.

However, Patent Document 1 (JP 2005-278742A) does not disclose any contrivance regarding washing and/or disinfecting the storage portion (working tank) storing the transmission liquid (working liquid). For example, a power source portion (an electrode that is to be connected to an external connection terminal of a main body) of an atomizer is provided in a recessed portion. For this reason, if the entirety of the atomizer is cleaned, water will accumulate in the recessed portion, and there is a possibility that an inconvenience such as rusting or corrosion of the electrode will occur.

In view of this, it is an object of the present invention to provide an ultrasonic nebulizer including a working tank that is configured to be detachable with respect to a main body, the ultrasonic nebulizer being able to prevent an inconvenience related to electrodes (referred to as "tank-side contact electrodes") of the working tank when a user (a doctor, nurse, or the like) cleans and/or disinfects the working tank.

Solution to the Problem

In order to solve the foregoing problems, an ultrasonic nebulizer of the present invention includes:

a working tank in which an ultrasonic vibrator is incorporated and in which a working liquid is stored facing the ultrasonic vibrator;

a medicine tank that stores a medicinal liquid, at least a bottom portion thereof being dipped in the working liquid; and a main body that includes an oscillation circuit that is to drive the ultrasonic vibrator, and main body-side contact electrodes that are to emit an output of the oscillation circuit, wherein the medicine tank is configured to be detachable with respect to the working tank, the working tank is configured to be detachable with respect to the main body, the working tank includes rod-shaped tank-side contact electrodes that extend in a vertical direction along an outer wall of the working tank, specific portions corresponding to portions in a circumferential direction of outer circumferential surfaces of the tank-side contact electrodes are exposed from the outer wall, and the remaining portions other than the specific portions in the circumferential direction of the outer circumferential surfaces of the tank-side contact electrodes are embedded inside of the outer wall and are connected to electrodes of the ultrasonic vibrator, and when the working tank is mounted on the main body, the main body-side contact electrodes come into contact with the specific portions of the outer circumferential surfaces of the tank-side contact electrodes.

In the present specification, the "working liquid" need only be a medium through which ultrasonic vibration can be transmitted, and water is typically used thereas. Examples of the medicinal liquid are not particularly limited and include a saline solution or a liquid mixture of a saline solution and Bisolvon.

Also, the medicine tank being configured to be "detachable" with respect to the working tank means that the medicine tank has a form in which the medicine tank can be mounted on the working tank and the medicine tank has a form in which the medicine tank can be removed from the working tank.

Similarly, the working tank being "configured to be detachable" with respect to the main body means that the shapes of the main body and the working tank are shapes according to which the working tank can be mounted on the main body and the working tank can be removed from the main body.

Also, the "vertical direction" in which the tank-side contact electrodes extend means a direction in which the tank-side contact electrodes extend when the working tank is in an upright orientation (the original orientation of being open upward).

With the ultrasonic nebulizer of the present invention, the output of the oscillation circuit is applied from the main body to the electrodes of the ultrasonic vibrator through the main body-side contact electrodes and the tank-side contact electrodes in a state in which at least the bottom portion of the medicine tank is dipped in the working liquid in the working tank. Accordingly, ultrasonic vibration generated by the ultrasonic vibrator is transmitted to the medicine tank via the working liquid in the working tank, and the medicinal liquid in the medicine tank is atomized.

As described above, from a hygienic viewpoint such as preventing the risk of infection, it is desirable to periodically wash and/or disinfect the working tank that stores the working liquid. In view of this, in the ultrasonic nebulizer of this invention, the medicine tank is configured to be detachable with respect to the working tank, and the working tank is configured to be detachable with respect to the main body. Accordingly, in a state in which the working tank and the medicine tank are mounted on the main body, for example, the user (a doctor, nurse, or the like) can easily take out only the working tank by first removing the working tank along with the medicine tank from the main body and then removing the medicine tank from the working tank. Alternatively, in a state in which the working tank and the medicine tank are mounted on the main body, the user can easily take out only the working tank by first removing the medicine tank from the working tank, and then removing the working tank from the main body. Accordingly, it is possible to easily wash and/or disinfect the working tank separately. The medicine tank can also be easily cleaned and/or disinfected with a disinfecting liquid separately. Moreover, the tank-side contact electrodes are rod-shaped and extend in the vertical direction along the outer wall of the working tank. Accordingly, if the working tank is put in the upright orientation after the entirety of the working tank is washed, water does not remain in the specific portion of the tank-side contact electrode that is exposed from the outer wall, and the water falls downward. As a result, inconveniences such as rusting or corrosion of the tank-side contact electrodes due to accumulated water do not occur.

Also, with the tank-side contact electrodes, the specific portions corresponding to portions in the circumferential direction of the outer circumferential surfaces of the tank-side contact electrodes are exposed from the outer wall, and the remaining portions other than the specific portions in the circumferential direction of the outer circumferential surfaces of the tank-side contact electrodes are embedded inside the outer wall. Accordingly, the tank-side contact electrodes can be firmly held by the wall of the active tank.

With an ultrasonic nebulizer of an embodiment,
the main body includes a containing portion for surrounding and containing the working tank, and
the main body-side contact electrodes have elongated rod shapes, are contained so as to be able to slide in a lengthwise direction in lateral holes penetrating through a side wall of the containing portion, and are biased by elastic members, in an orientation in which leading ends thereof are exposed from the side wall in the lengthwise direction.

With the ultrasonic nebulizer of this embodiment, in the case where the working tank is to be mounted on the main body, the working tank is lowered in an upright orientation from above onto the containing portion of the main body. At this time, when the lower ends of the tank-side contact electrodes come into contact with the leading ends of the main body-side contact electrodes, the main body-side contact electrodes retract in the lengthwise direction against the biasing forces of the elastic members. Accordingly, even if the position of the working tank is slightly misaligned in a horizontal plane with that of the main body-side contact electrodes, lowering of the working tank is allowed due to the main body-side contact electrodes retracting. When the working tank is further lowered with respect to the main body, the specific portions of the outer circumferential surfaces of the tank-side contact electrodes enter a state of being in contact with the leading ends of the main body-side contact electrodes. In this manner, the working tank is smoothly mounted on the main body. Also, even if debris or dust attaches to the specific portion of the outer circumferential surfaces of the tank-side contact electrodes, the debris or dust is wiped off due to the specific portions of the outer circumferential surfaces of the tank-side contact electrodes sliding against the leading ends of the main-body side contact electrodes when they are lowered (wiping effect). Also, in the state in which the working tank is mounted on the main body, the leading ends of the main body-side contact electrodes are pressed to the specific portions of the outer circumferential surfaces of the tank-side contact electrodes due to the biasing forces of the elastic members. Accordingly, favorable connections are obtained between the main body-side contact electrodes and the tank-side contact electrodes.

With an ultrasonic nebulizer of an embodiment,
the tank-side contact electrodes are provided at portions on mutually opposite sides of the outer wall of the working tank, and
the main body-side contact electrodes are provided facing each other in a horizontal direction on the side wall of the containing portion.

With the ultrasonic nebulizer of this embodiment, the main body-side contact electrodes are provided facing each other in the horizontal direction on the side wall of the containing portion, and therefore, when the working tank is lowered into the containing portion of the main body, the degree of allowing positional misalignment in the horizontal plane of the working tank increases accordingly. Also, in the state in which the working tank is mounted on the main body, the main body-side contact electrodes provided facing each other press the working tank, and therefore the working tank is positioned in the horizontal plane.

With an ultrasonic nebulizer of an embodiment, the tank-side contact electrodes have circular rod shapes.

With the ultrasonic nebulizer of this embodiment, since the tank-side contact electrodes are circular rod-shaped, a property of sealing out the water or the disinfecting liquid can be easily realized between the tank-side contact electrodes and the wall surrounding the tank-side contact electrodes by fitting the O rings on the tank-side contact electrodes. In the case of doing so, even if the entirety of the working tank is washed and/or disinfected, it is possible to prevent the water or disinfecting liquid from entering the internal structure of the working tank (e.g., the gap in which the ultrasonic vibrator is incorporated). Also, if the tank-side contact electrodes are in the form of circular rods, machining is easy in the manufacturing step.

With an ultrasonic nebulizer of an embodiment,
first tapered surfaces that are tapered are provided on lower ends of the tank-side contact electrodes, and
second tapered surfaces that are tapered are provided on leading ends of the main body-side contact electrodes.

In the present specification, the "lower ends" of the tank-side contact electrodes mean the end portions on the side that is downward when the working tank is in the upright orientation, among the ends of the tank-side contact electrodes.

With the ultrasonic nebulizer of this embodiment, first tapered surfaces that are tapered are provided on the lower ends of the tank-side contact electrodes, and second tapered surfaces that are tapered are provided on the leading ends of the main body-side contact electrodes. Accordingly, when the working tank is lowered onto the main body, the degree of permitting positional misalignment in a horizontal plane of the working tank is further increased.

With an ultrasonic nebulizer of an embodiment, the entire circumference of the outer circumferential surface of an upper portion of each tank-side contact electrode is embedded inside the outer wall, and O rings are fit into the upper portions of the tank-side contact electrodes so as to provide a sealing property between the upper portions of the tank-side contact electrodes and a wall of the working tank that surrounds the upper portions.

With the ultrasonic nebulizer of this embodiment, the property of sealing is realized between the upper portions of the tank-side contact electrodes and the wall of the working tank that surrounds the upper portions. Accordingly, even if the entirety of the working tank is washed and/or disinfected, the water or disinfecting liquid can be prevented from entering the internal structure of the working tank (e.g., the gap in which the ultrasonic vibrator is incorporated).

With an ultrasonic nebulizer of an embodiment, ring-shaped grooves that wrap around portions above the O rings of the upper portions of the tank-side contact electrodes are formed at those portions, and the tank-side contact electrodes are connected to the electrodes of the ultrasonic vibrator via E rings that are press-fit into the ring-shaped grooves.

With the ultrasonic nebulizer of this embodiment, ring-shaped grooves that wrap around portions located above the O rings on the upper portions of the tank-side contact electrodes are formed at those portions. Also, the tank-side contact electrodes are connected to the electrodes of the ultrasonic vibrator via E-rings that are press-fit into the ring-shaped grooves. Accordingly, the tank-side contact electrodes and the electrodes of the ultrasonic vibrator are favorably connected without soldering the tank-side contact electrodes.

With an ultrasonic nebulizer of an embodiment, lower ends of the tank-side contact electrodes are located above the lowest portions of the working tank.

With the ultrasonic nebulizer of this embodiment, the lower ends of the tank-side contact electrodes are located above the lowest portions of the working tank. Accordingly, even if the user places the working tank on a platform that is wet with a liquid such as water or the disinfecting liquid, the lower ends of the tank-side contact electrodes do not get wet. Accordingly, it is possible to avoid a situation that causes short-circuiting between the tank-side contact electrodes or electrical leakage.

With an ultrasonic nebulizer of an embodiment, the tank-side contact electrodes are made of titanium.

With the ultrasonic nebulizer of this embodiment, the tank-side contact electrode is made of titanium, and therefore even if the working tank is immersed in a disinfecting liquid such as an aqueous solution of sodium hypochlorite, an inconvenience such as the exposed specific portion of the tank-side contact electrode rusting or corroding does not occur.

Advantageous Effects of the Invention

As is clear from the above description, according to the ultrasonic nebulizer of the present invention, in an ultrasonic nebulizer including a working tank that is configured to be detachable with respect to a main body, it is possible to prevent an inconvenience related to the electrode of the working tank when the user washes and/or disinfects the working tank.

DESCRIPTION OF EMBODIMENTS

Hereinafter, embodiments of the present invention will be described in detail with reference to the drawings.

Figure 1:
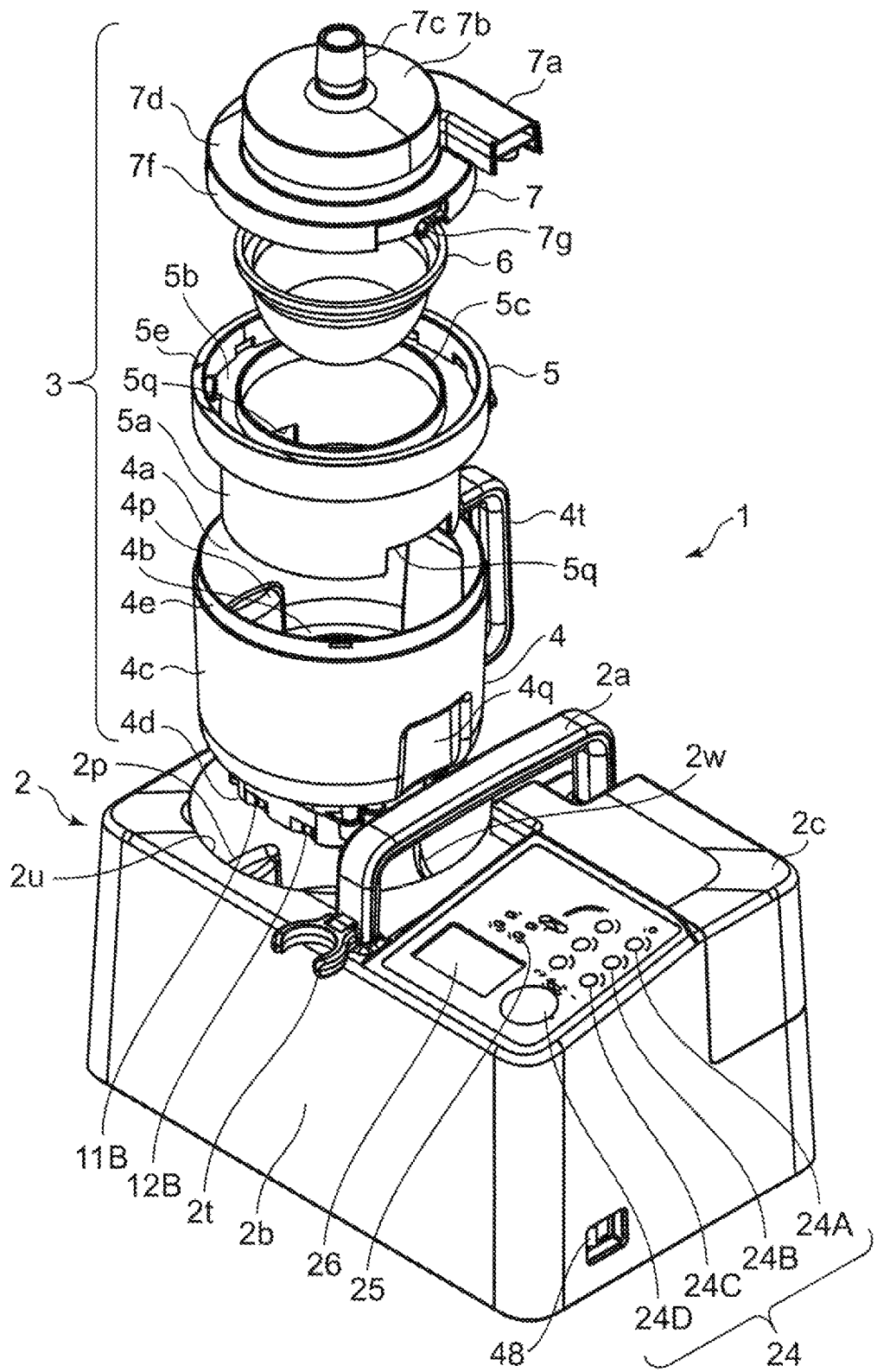
FIG. 1 is a diagram showing an exploded view from above and obliquely to the right of an ultrasonic nebulizer of an embodiment of the invention.
Figure 2:
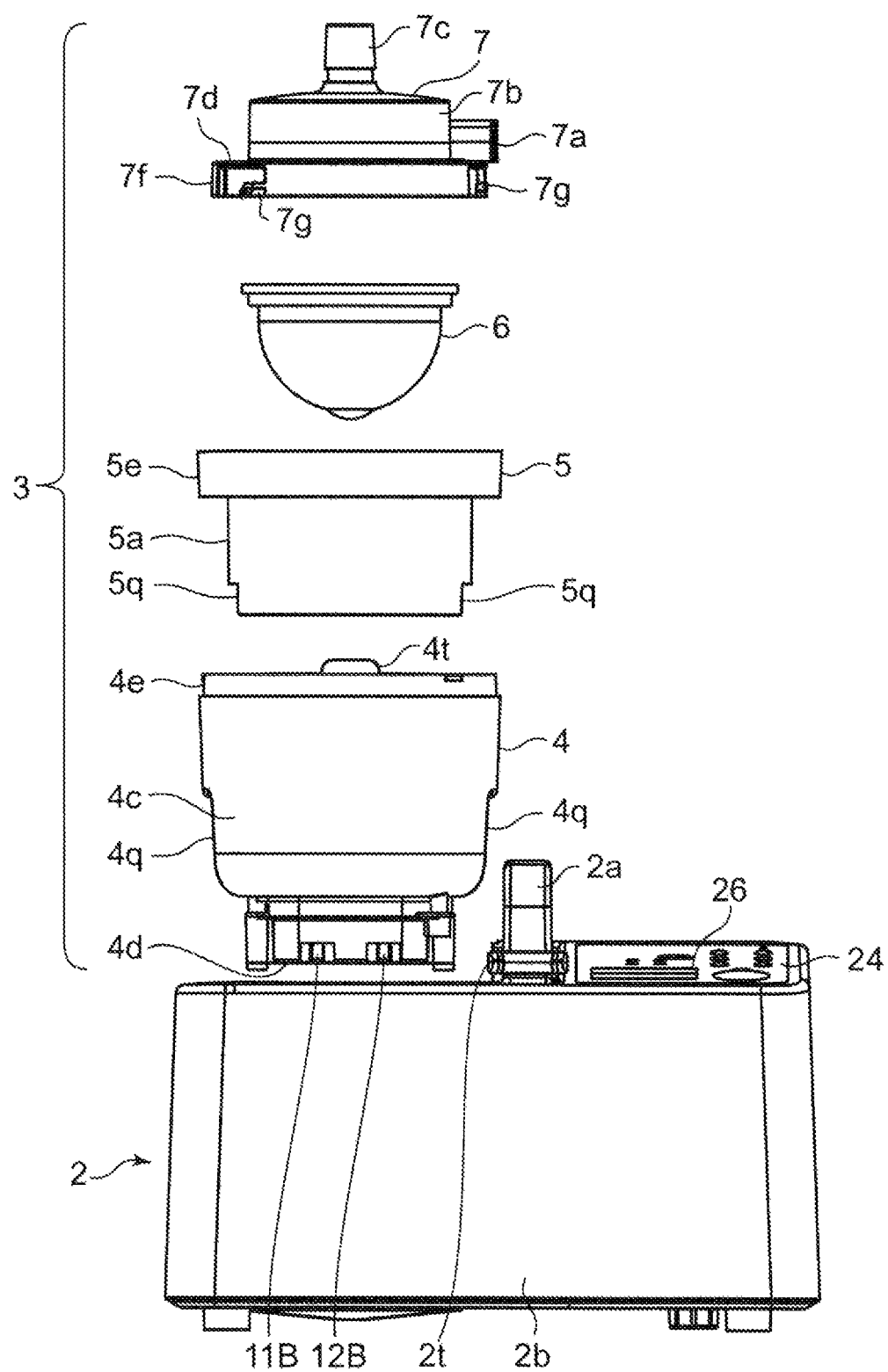
FIG. 2 is a diagram showing a view from the front of the ultrasonic nebulizer shown in FIG. 1.

FIG. 1 shows an exploded view from above and obliquely to the right of an ultrasonic nebulizer (indicated overall by reference numeral 1) of an embodiment of the invention. FIG. 2 shows a view from the front of the ultrasonic nebulizer 1 shown in FIG. 1.

As can be understood from FIGS. 1 and 2, the ultrasonic nebulizer 1 generally includes a main body 2 and a tank unit 3 that is configured to be detachable with respect to the main body 2.

The tank unit 3 includes a working tank 4, a medicine tank support 5, a medicine tank 6, and a medicine tank cover 7. The elements 4, 5, 6, and 7 of the tank unit 3 can be assembled by being overlaid in the stated order in a fit-together manner by the hand of a person without need for a tool, and can be disassembled in the inverse order.

The main body 2 includes a main portion 2b that forms a housing, and a carrying handle 2a that is provided on the upper surface of the main portion 2b and extends in the front-rear direction. An approximately cylindrical containing portion 2u for surrounding and containing the tank unit 3 is provided in the left half of the main portion 2b (leftward of the handle 2a). An opening 2w that is continuous with the containing portion 2u is provided on the rear surface side of the main portion 2b. The width (dimension in the left-right direction) of the opening 2w is set to be a dimension large enough that a person's fist can be inserted therein, for the sake of convenience in mounting the tank unit 3. A seating platform portion 2d (see FIGS. 3 and 4) on which the tank unit 3 is to be mounted is provided at the bottom of the containing portion 2u (below the main portion 2b). As shown in FIGS. 1 and 2, a C-shaped hose holder 2t for holding the leading end portion of an air suction hose 8 (see FIG. 9) attached to the medicine tank cover 7 is provided on the front portion of the handle 2a.

An operation switch portion 24, an LED (light-emitting diode) display unit 25, and an LCD (liquid crystal display element) display unit 26 are provided on the right half of the upper surface of the main body 2 (rightward of the handle 2a). The operation switch portion 24 includes a timer adjustment key switch 24A by which the user (a doctor, a nurse, or the like) inputs a continuous spray time, an air flow adjustment key switch 24B, which serves as a first operation portion and is for inputting an air flow setting value, an atomization amount adjustment key switch 24C, which serves as a second operation portion and is for inputting an atomization amount setting value, and a spraying start/stop switch 24D for instructing the start or stopping of spraying. Note that the key switches 24A, 24B, and 24C each include an up key and a down key (indicated by the left and right pairs of circular marks in FIGS. 1 and 2) for increasing and reducing the input values. The LED display unit 25 and the LCD display unit 26 receive and display signals indicating the atomization amount, the air flow, the timer, the start of spraying, and states such as error from the later-described CPU 28 (see FIG. 9).

As shown in FIG. 1, a power switch 48 for the ultrasonic nebulizer 1 is provided on the right-side surface of the main body 2. Also, an air cover 2c that covers a later-described air fan is provided on the right rear portion of the main body 2.

Figure 5:
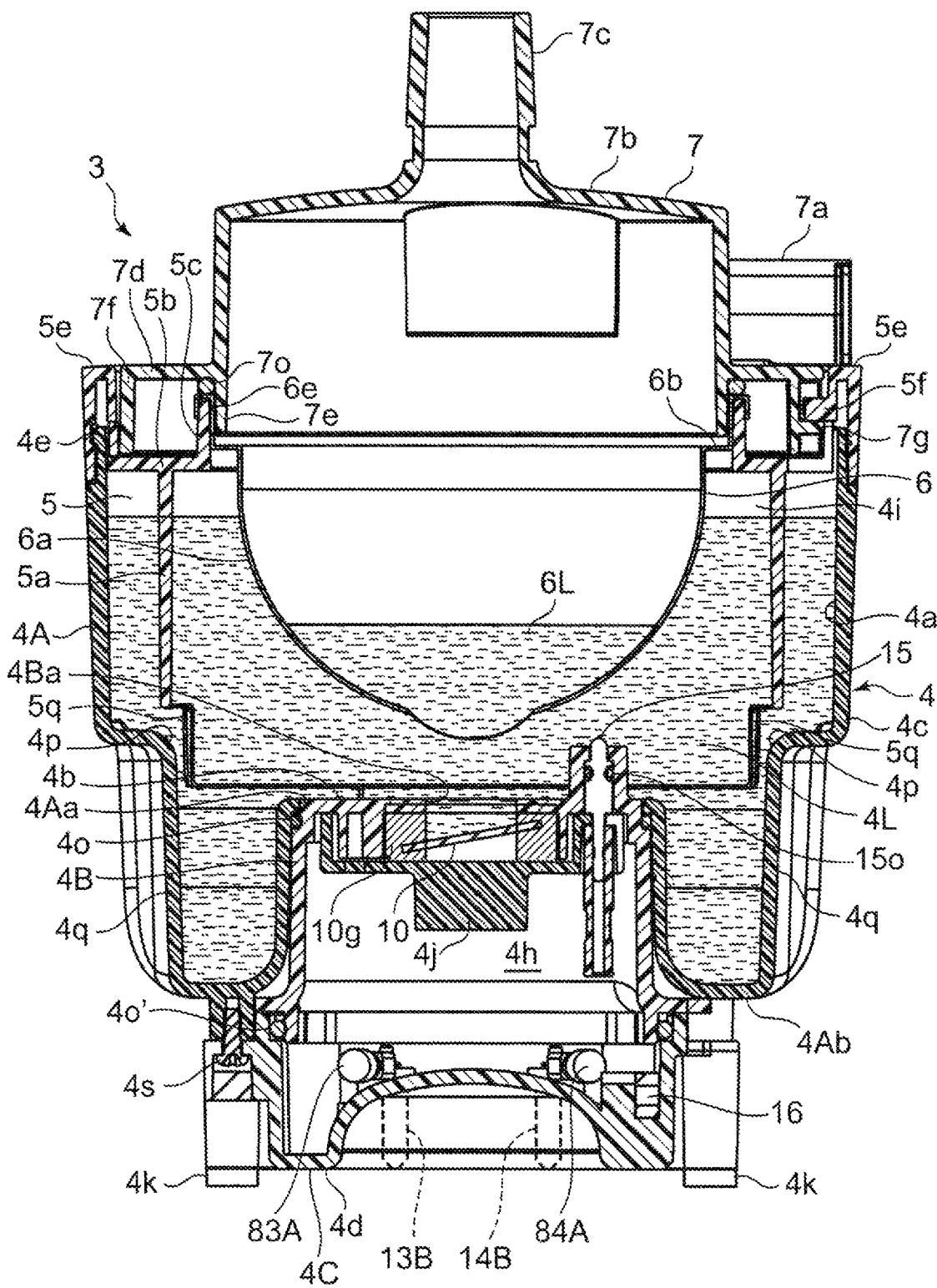
FIG. 5 is a longitudinal cross-sectional view (a cross-sectional view parallel to the surface of the page in FIG. 2) showing a configuration of the tank unit included in the ultrasonic nebulizer.
Figure 6:
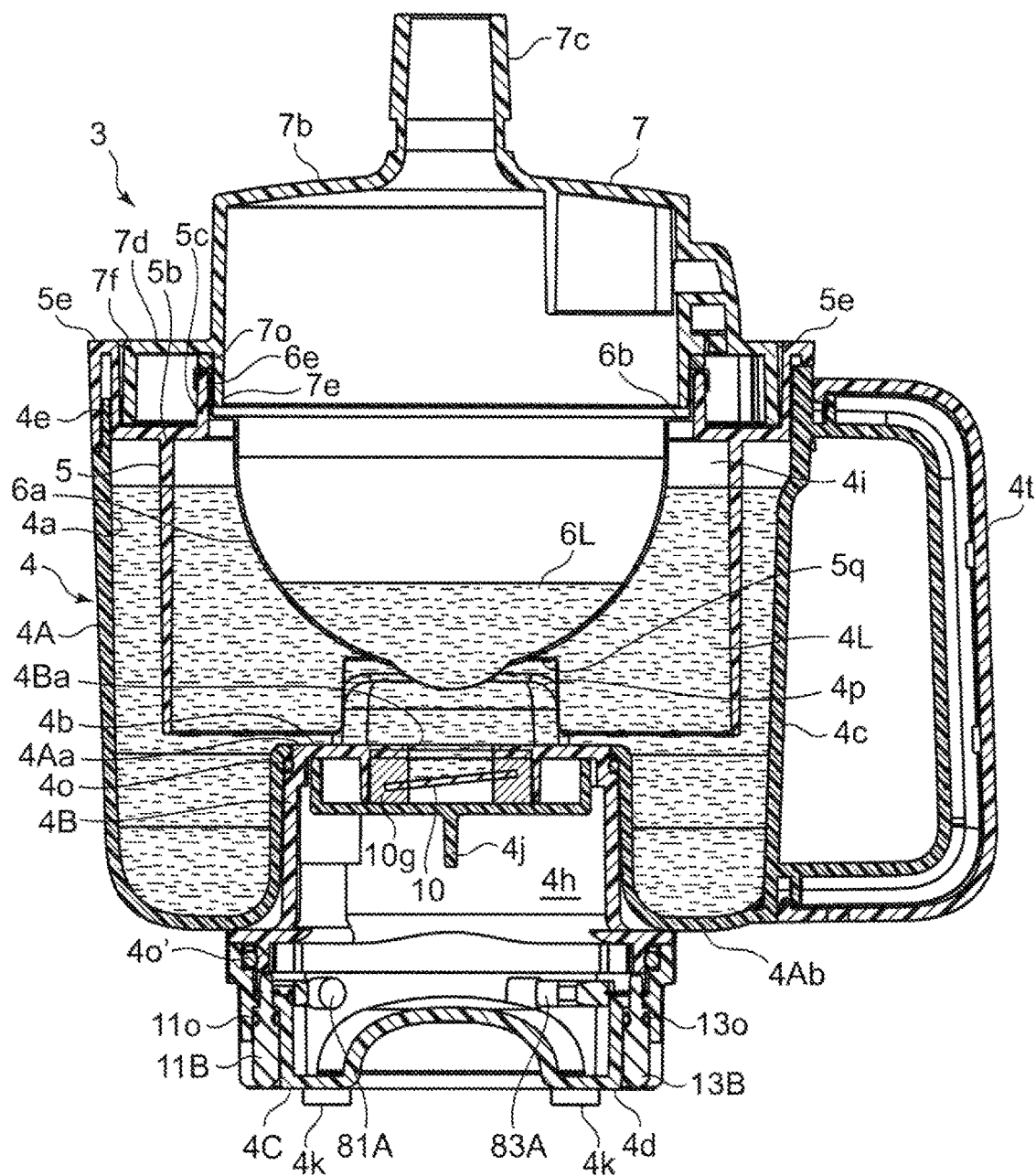
FIG. 6 is another longitudinal cross-sectional view (a cross-sectional view orthogonal to the surface of the page in FIG. 2) showing the configuration of the tank unit.

FIG. 5 shows a longitudinal cross section taken parallel to the page surface of FIG. 2, of the tank unit 3, which is in an assembled state. FIG. 6 shows a longitudinal cross section taken perpendicular to the page surface of FIG. 2, of the tank unit 3 in such a state.

As can be understood from FIGS. 5 and 6, the working tank 4 is open upward and includes: an approximately cylindrical inner circumferential wall 4a; an inner bottom surface 4b that covers the lower portion of the inner circumferential wall 4a; an approximately cylindrical outer circumferential wall 4c that wraps around the inner circumferential wall 4a; an outer bottom surface 4d that covers the lower portion of the outer circumferential wall 4c; a top portion 4e that connects the upper edge of the inner circumferential wall 4a and the upper edge of the outer circumferential wall 4c; and a carrying handle 4t that is attached in an integrated manner to the outer circumferential wall 4c. A working liquid (in this example, water) 4L is contained in a tank inner space 4i, which is formed by the inner circumferential wall 4a and the inner bottom surface 4b, which constitute the inner surface of the working tank 4. A gap 4h is provided between the inner bottom surface 4b and the outer bottom surface 4d. Accordingly, the working tank 4 has a double-bottomed structure.

More specifically, the working tank 4 is mainly (aside from the handle 4) constituted by a first member 4A composed of ABS (acrylonitrile butadiene styrene copolymer) resin, which forms the inner circumferential wall 4a and the outer circumferential wall 4c, a second member 4B composed of PPS (polyphenylene sulfide) resin, which forms the inner bottom surface 4b, and a third member 4C composed of PPS resin, which forms the outer bottom surface 4d. The first member 4A has an approximately cylindrical shape, has a lower portion 4Ab that is curved so as to protrude downward, and has an approximately circular opening 4Aa that is formed in a rising manner on the inner side. The second member 4B has an approximately cylindrical shape and the upper portion thereof fits watertightly into the opening 4Aa of the first member 4A via an O ring 4o. The upper portion of the second member 4B forms the inner bottom surface 4b of the working tank 4. An opening 4Ba is formed in the inner bottom surface 4b of the working tank 4 (second member 4B). The third member 4C has an approximately square tube-shaped outer shape and the upper portion thereof is fit watertightly around the lower portion of the second member 4B via an O ring 4o'. The lower portion of the third member 4C is closed and forms the outer bottom surface 4d of the working tank 4. The third member 4C is attached to the lower portion 4Ab of the first member 4A using multiple screws 4s (only one is shown in FIG. 5). As a result, the working tank 4 is integrally assembled in a state in which the second member 4B is interposed between the first member 4A and the third member 4C. Note that legs 4k of the working tank 4 are provided in a downwardly-projecting manner on the outer bottom surface 4d (third member 4C).

A plate-shaped ultrasonic vibrator 10 is incorporated in the gap 4h that forms the double-bottomed structure of the working tank 4. The vibrating surface of the ultrasonic vibrator 10 is arranged so as to face the tank inner space 4i from below the inner bottom surface 4b, through the opening 4Ba provided in the inner bottom surface 4b. More specifically, the ultrasonic vibrator 10 is held by being fit in a frame-shaped rubber holder 10g. The rubber holder 10g is pressed onto the periphery of the opening 4Ba of the inner bottom surface 4b from below by a pressing member 4j that is attached by a screw (not shown) to the inner bottom surface 4b. Accordingly, together with the holder 10g, the ultrasonic vibrator 10 is incorporated in a state in which the working liquid 4L does not leak from the tank inner space 4i through the opening 4Ba.

Also, a liquid level sensor 15 for detecting the liquid surface of the working liquid 4L is arranged at a predetermined height level of the tank inner space 4i. The liquid level sensor 15 generates a voltage signal that indicates whether or not the liquid level of the working liquid 4L in the working tank 4 exceeds the height level (necessary level). The liquid level sensor 15 is attached watertightly with an O ring 15o, penetrating through the inner bottom surface 4b. Furthermore, a magnet 16 that is to be used to detect whether or not the working tank 4 has been mounted on the main body 2 is incorporated in the gap 4h.

Figure 14:
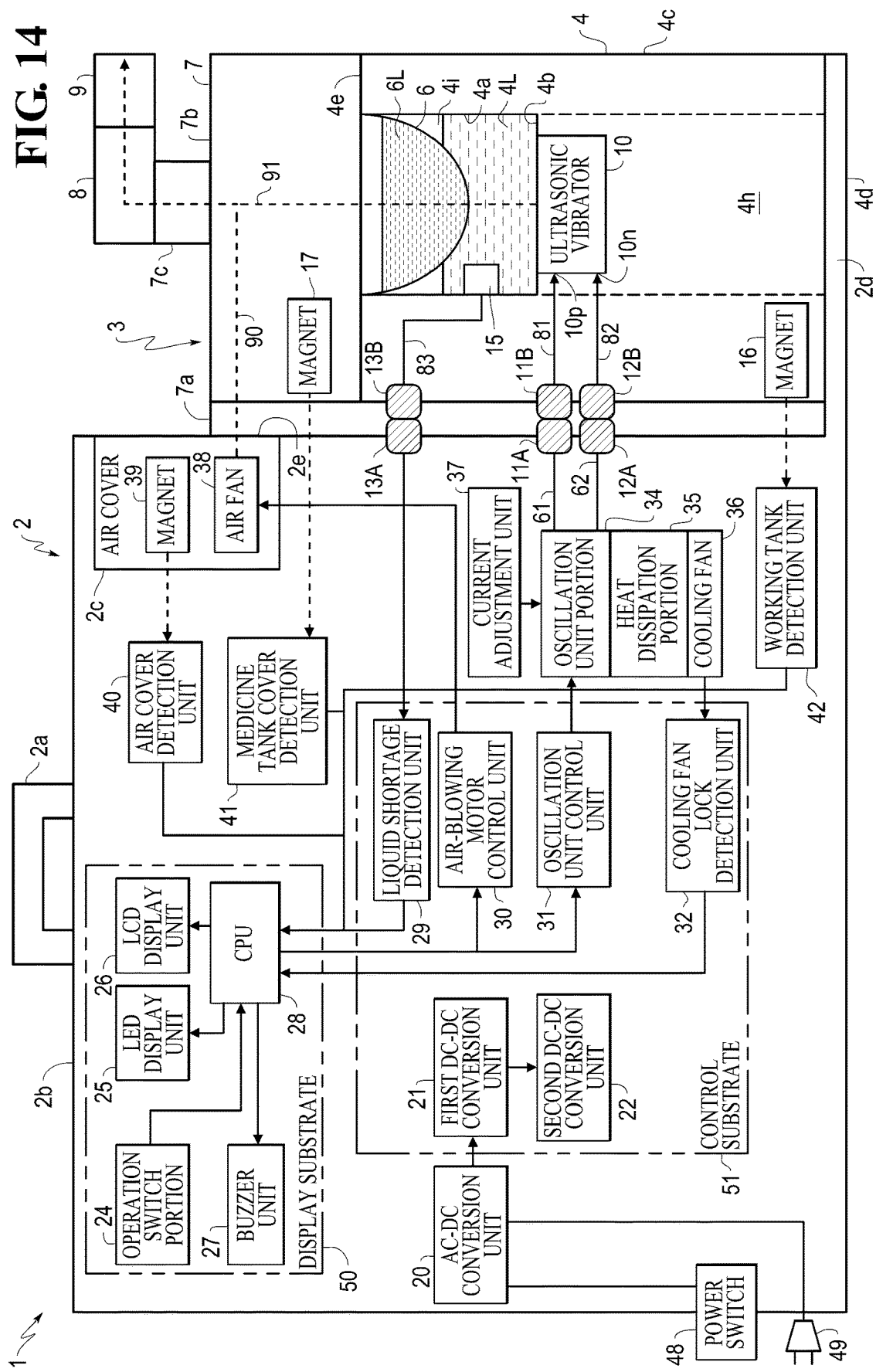
FIG. 14 is a diagram showing a schematic block configuration of the ultrasonic nebulizer.

In this example, first, second, third, and fourth tank-side contact electrodes 11B, 12B, 13B, and 14B are provided on the bottom portion (third member 4C) of the working tank 4 so as to penetrate through the outer wall (FIGS. 1 and 2 show the first and second tank-side contact electrodes 11B and 12B on the front surface side of the working tank 4, FIG. 5 shows the third and fourth tank-side contact electrodes 13B and 14B on the rear surface side of the working tank 4, and FIG. 6 shows the first and third tank-side contact electrodes 11B and 13B; the first and second tank-side contact electrodes 11B and 12B, which form a pair on the front surface side are provided respectively facing the third and fourth tank-side contact electrodes 13B and 14, which form a pair on the rear surface side). The tank-side contact electrodes 11B, 12B, 13B, and 14B are attached watertightly to the outer wall with O rings (FIG. 6 shows O rings 11$o$ and 13$o$ that correspond to the first and third tank-side contact electrodes 11B and 13B). As shown in FIG. 14, the first and second tank-side contact electrodes 11B and 12B are connected to first and second electrodes 10$p$ and 10$n$ of the ultrasonic vibrator 10 by wires 81 and 82, respectively. Also, the third tank-side contact electrode 13B is connected to the liquid level sensor 15 by a wire 83. Note that metal members 81A and 83A in FIGS. 5 and 6 form portions of the wires 81 and 83. A metal member 84A is connected to a fourth tank-side contact electrode (dummy tank-side contact electrode) 14B.

Note that as shown in FIGS. 1 and 2 as well as FIGS. 5 and 6, with the working tank 4, specific locations (a left and right pair of locations in a view from the front) are curved toward the tank interior with respect to the circumferential direction of the first member 4A. Accordingly, a left and right pair of recesses 4$q$ and 4$q$ are formed in the outer circumferential wall 4$c$. Also, a left and right pair of protrusions 4$p$ and 4$p$ are formed in the inner circumferential wall 4$a$. The recesses 4$q$ and 4$q$ are used to guide the tank unit 3 (working tank 4) when the tank unit 3 (working tank 4) is mounted on the main body 2 (main portion 2$b$). The protrusions 4$p$ and 4$p$ are used to fix the orientation (direction) of the medicine tank support 5 with respect to the working tank 4.

As shown in FIGS. 1 and 2 as well as FIGS. 5 and 6, the medicine tank support 5 includes: a cylindrical portion 5$a$ that is contained in the tank inner space 4$i$ of the working tank 4, a flat support portion 5$b$ that is provided along the upper end of the cylindrical portion 5$a$, an engagement portion 5$e$ that is provided along the outer edge of the support portion 5$b$ and opens downward with a C-shaped cross-section, and a projection portion 5$c$ that is provided along the inner edge of the support portion 5$b$ and projects upward. Cut-outs 5$q$ and 5$q$ that open downward in C shapes are formed at specific locations (a left and right pair of locations in a view from the front) with respect to the circumferential direction of the cylindrical portion 5$a$. As shown in FIGS. 5 and 6, the medicine tank support 5 is arranged overlaid on the working tank 4 from above due to the engagement portion 5$e$ fitting into the top portion 4$e$ of the working tank 4. At this time, the orientation (direction) of the medicine tank support 5 is fixed with respect to the working tank 4 by matching the cut-outs 5$q$ with the projections 4$p$ of the working tank 4. Conversely, if the medicine tank support 5 is pulled upward off of the working tank 4, the medicine tank support 5 is removed from the working tank 4. Note that in the medicine tank support 5, a projection 5$f$ for locking the medicine tank cover 7 is provided at a specific location with respect to the circumferential direction on the inner side of the engaging portions 5$e$.

The medicine tank 6 includes a main portion 6$a$ that is formed so as to protrude downward in an approximate hemispherical shape, a flat step portion 6$b$ that is provided along the upper end of the main portion 6$a$, and an engagement portion 6$e$ that is provided along the outer edge of the step portion 6$b$ and opens downward with a C-shaped cross-section. Due to the engagement portion 6$e$ fitting onto the projection portion 5$c$ of the medicine tank support 5, the medicine tank 6 is arranged overlaid on the medicine tank support 5 from above. Conversely, if the medicine tank 6 is pulled upward off of the medicine tank support 5, the medicine tank 6 is removed from the medicine tank support 5. A medicinal liquid 6L that is to be atomized is contained in the medicine tank 6. Examples of the medicinal liquid 6L include a saline solution or a liquid mixture of a saline solution and Bisolvon. When the tank unit 3 is assembled, the bottom portion of the medicine tank 6 is dipped in the working liquid 4L in the working tank 4.

Figure 7:
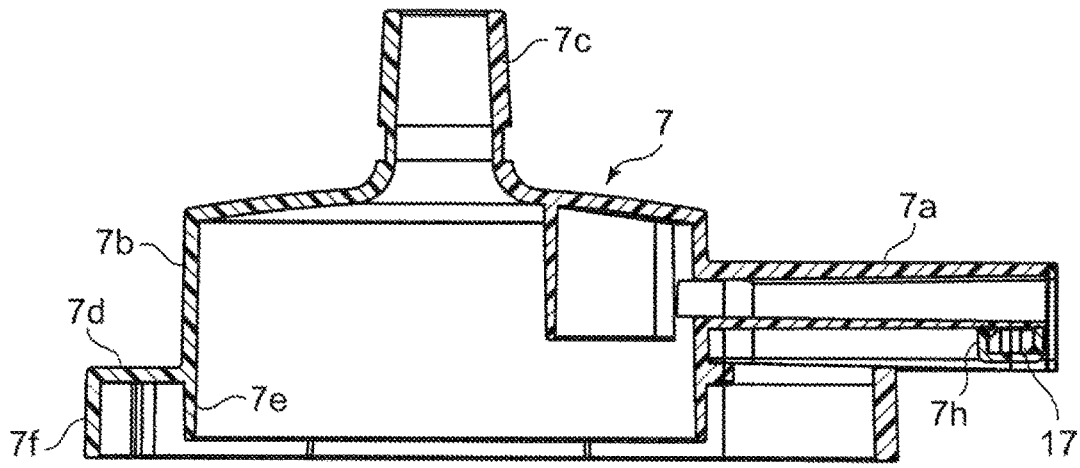
FIG. 7 is a cross-sectional view showing a configuration of a medicine tank cover included in the tank unit.

As shown in FIGS. 5 and 6, as well as in FIG. 7, which shows only the medicine tank cover 7, the medicine tank cover 7 includes: a simple cylindrical cover portion 7$b$ with an upper portion that is closed so as to cover the upper portion of the medicine tank 6; an air duct 7$a$ that is in communication with the cover portion 7$b$ and extends laterally; and an emission port 7$c$ that is in communication with the cover portion 7$b$ and extends upward. Also, a flat flange portion 7$d$ is formed along the periphery of the cover portion 7$b$. Furthermore, a ring-shaped outer edge portion 7$f$ that projects downward is formed along the outer edge of the flange portion 7$d$. As shown in FIG. 7, together with a magnet attachment case 7$h$, a magnet 17 that is to be used to detect whether or not the medicine tank cover 7 has been mounted correctly on the main body 2 is incorporated on the lower portion of the entrance to the air duct 7$a$.

As shown in FIGS. 1, 2, and 5, an engagement portion 7$g$ that is to be locked on the engagement portion 5$e$ of the medicine tank support 5 is formed at a specific location with respect to the circumferential direction of the outer edge portion 7$f$ on the medicine tank cover 7. As shown in FIGS. 5 and 6, the medicine tank cover 7 is arranged overlaid on the medicine tank 6 from above in a state in which an O ring 7$o$ is attached around a lower portion 7$e$ of the cover portion 7$b$. More specifically, the engagement portion 6$e$ of the medicine tank 6 is pressed from above by the medicine tank cover 7 via the O ring 7$o$. Along with this, the engagement portion 7$g$ is locked by passing below the projection 5$f$ of the medicine tank support 5 due to the medicine tank cover 7 being rotated (in this example, clockwise in a view from above) slightly about the center (in the perpendicular direction) of the cover portion 7$b$. Accordingly, the medicine tank cover 7 is attached to the medicine tank support 5 in a mode in which the engagement portion 6$e$ of the medicine tank 6 is interposed between the medicine tank cover 7 and the projecting portion 5$c$ of the medicine tank support 5 via the O ring 7$o$, and the air duct 7$a$ of the medicine tank cover 7 is arranged in a predetermined orientation (direction) with respect to the working tank 4 (the handle 4$t$ of the working tank 4). In this example, in a view directly facing the handle 4$t$ of the working tank 4, the entrance of the air duct 7$a$ of the medicine tank cover 7 is arranged so as to face leftward. Conversely, if the medicine tank cover 7 is rotated slightly counterclockwise about the center of the cover portion 7$b$ and the medicine tank cover 7 is pulled upward, the medicine tank cover 7 is removed.

Figure 3:
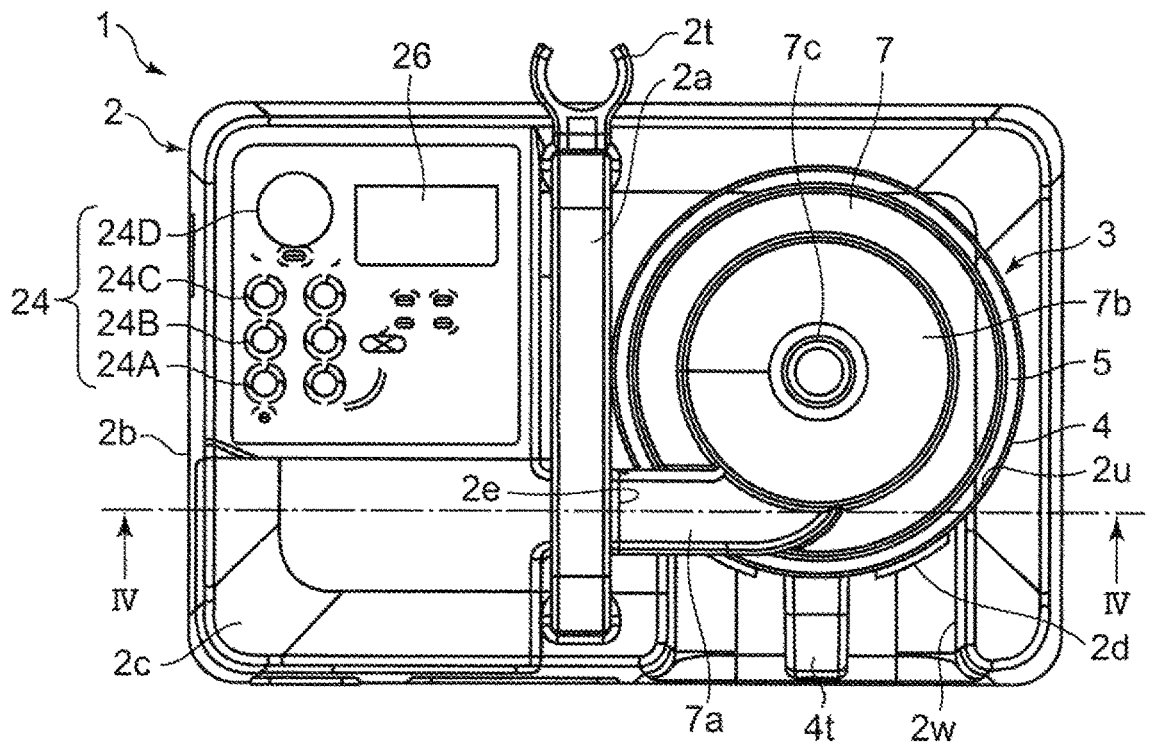
FIG. 3 is a diagram showing a view from above of the ultrasonic nebulizer in a tank unit mounted state.

FIG. 3 shows a view from above of a state (tank unit mounted state) in which the tank unit 3 is mounted on the main body 2 (the front surface of the main body 2 is drawn above, and the rear surface is drawn below). Also, FIG. 4 shows a cross-sectional view taken along line IV-IV in FIG. 3 and viewed in the direction of the arrows.

Figure 4:
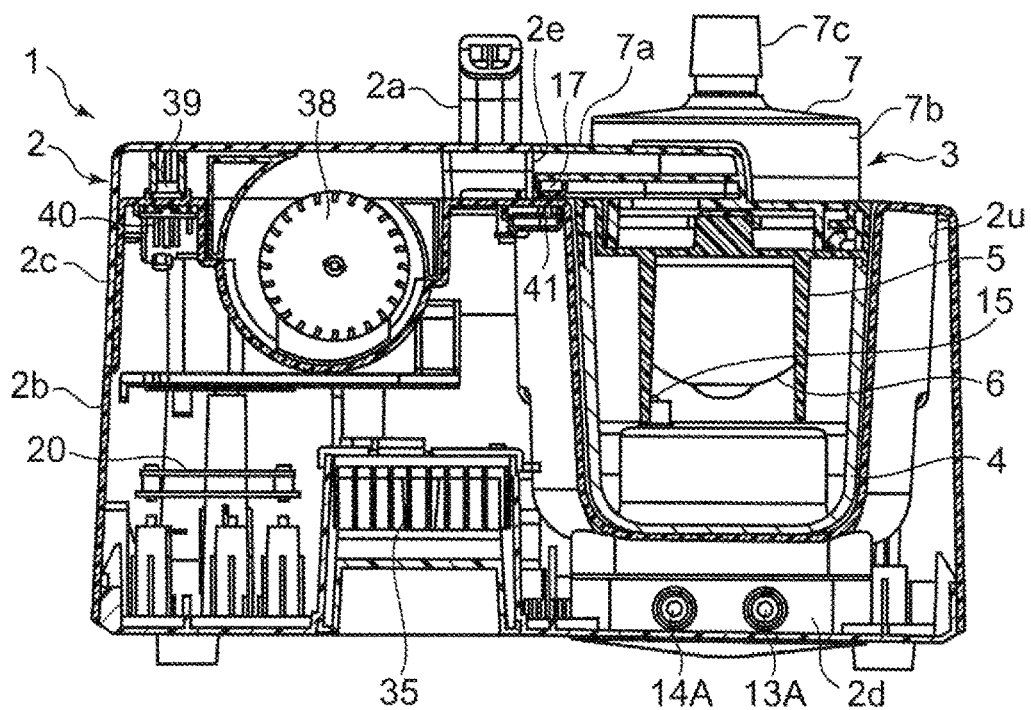
FIG. 4 is a diagram showing a cross-sectional view taken along line IV-IV in FIG. 3 and viewed in the direction of the arrows.

As shown in FIGS. 3 and 4, in the tank unit mounted state, the tank unit 3 is attached on the seating platform portion 2$d$ on the bottom of the containing portion 2$u$ of the main body 2. The tank unit 3 is attached in a mode in which the handle 4$t$ of the working tank 4 faces rearward of the main body 2 and the outer side of the handle 4$t$ approximately matches the rear surface of the main body 2. An arrangement is used in which the entrance of the air duct 7$a$ of the medicine tank cover 7 extends above the main body 2 (main portion 2b). In the tank unit mounted state, the tank unit 3 is protected by being surrounded by the main body 2, and the tank unit 3 (particularly, the working tank 4) no longer detaches unexpectedly from the main body 2.

As shown in FIG. 4, an air fan (includes a motor that rotates the fan) 38 for blowing air to the medicine tank 6 is arranged on the upper portion of the main body 2 (main portion 2b). The air fan 38 is covered by an air cover 2c that can be detached from the main portion 2b. A vent 2e that communicates with the air duct 7a on the tank unit 3 side in the tank unit mounted state is provided in the air cover 2c. In the main portion 2b, a medicine tank cover detection unit 4l is provided at a location that corresponds to directly below the magnet 17 of the air duct 7a. The medicine tank cover detection unit 4l includes a hole IC (integrated circuit including a magnetic sensor) and uses the magnetic force of the magnet 17 incorporated in the medicine tank cover 7 to detect whether or not the medicine tank cover 7 has been correctly mounted on the main portion 2b (whether or not the air duct 7a matches the vent 2e).

Also, a magnet 39 that is used to detect whether or not the air cover 2c has been mounted on the main portion 2b is attached to the inner side of the air cover 2c. In the main portion 2b, the air cover detection unit 40 is provided at a location that corresponds to directly below the magnet 39 of the air cover 2c. The air cover detection unit 40 includes a hole IC and uses the magnetic force of the magnet 39 attached to the air cover 2c to detect whether or not the air cover 2c has been mounted on the main portion 2b.

A later-described AC-DC conversion unit 20 and a heat dispersion portion 35 are arranged in the lower portion in the main portion 2b.

Figure 8:
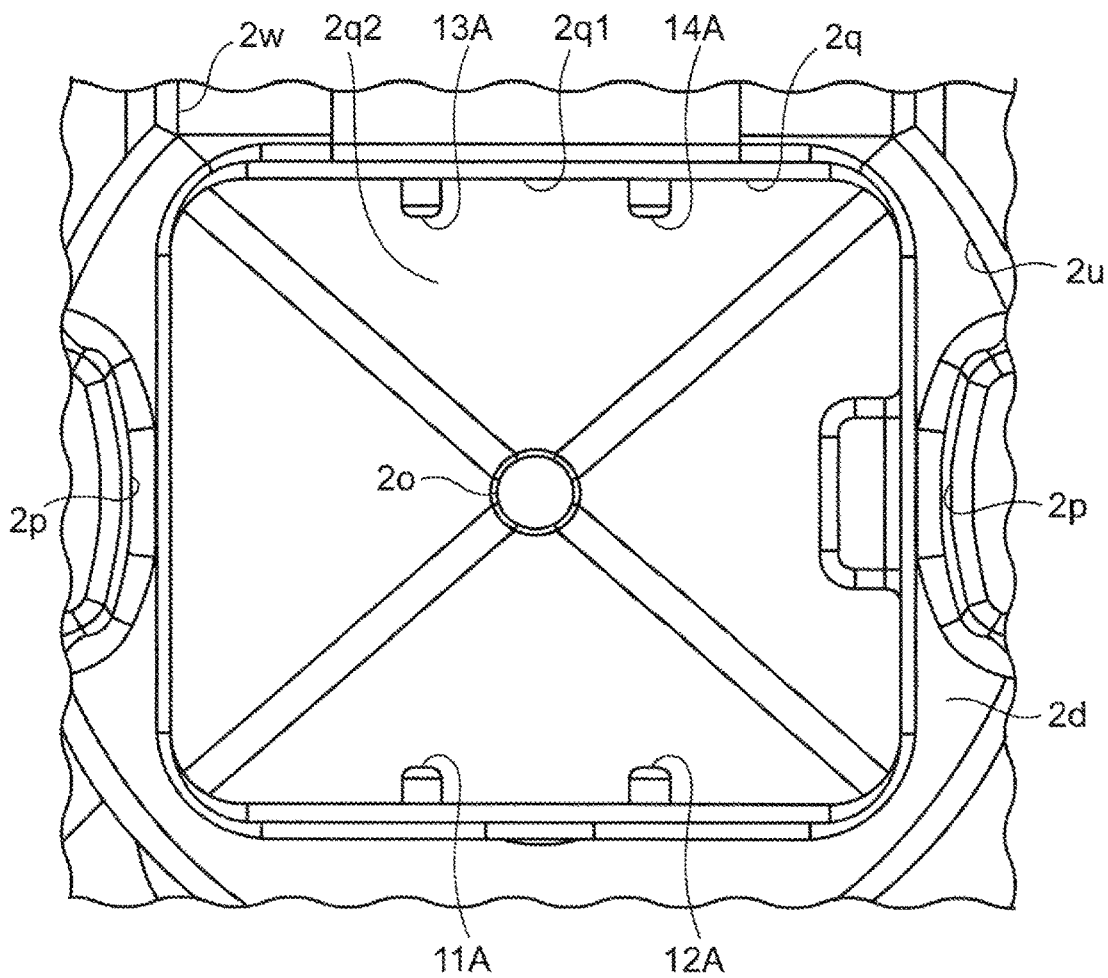
FIG. 8 is a diagram showing a view from above of a containing portion for containing the tank unit in the main body of the ultrasonic nebulizer.

FIG. 8 shows a view from above of the containing portion 2u for containing the tank unit 3 in the main body 2 (the front surface side of the main body 2 is drawn below and the rear surface side is drawn above). The protrusions 2p and 2p that are to be fit into the recesses 4q and 4q (see FIGS. 1 and 2) of the working tank 4 are formed at specific locations (a left and right pair of locations in a view from the front) with respect to the circumferential direction of the inner surface of the containing portion 2u. Approximately rectangular recesses 2q are formed on the seating platform portion 2d at the bottom of the containing portion 2u and the first, second, third, and fourth main body-side contact electrodes 11A, 12A, 13A, and 14A are provided so as to protrude from side walls 2q1 of the recesses 2q. The first, second, third, and fourth main body-side contact electrodes 11A, 12A, 13A, and 14A are made of titanium with an elongated, approximately circular rod shape, and are biased in an orientation of protruding from the side wall 2q1 due to coil springs, as will be described later. Note that if the first, second, third, and fourth main body-side contact electrodes 11A, 12A, 13A, and 14A are approximately circular rod-shaped, machining is easy in the manufacturing step.

Figure 11:
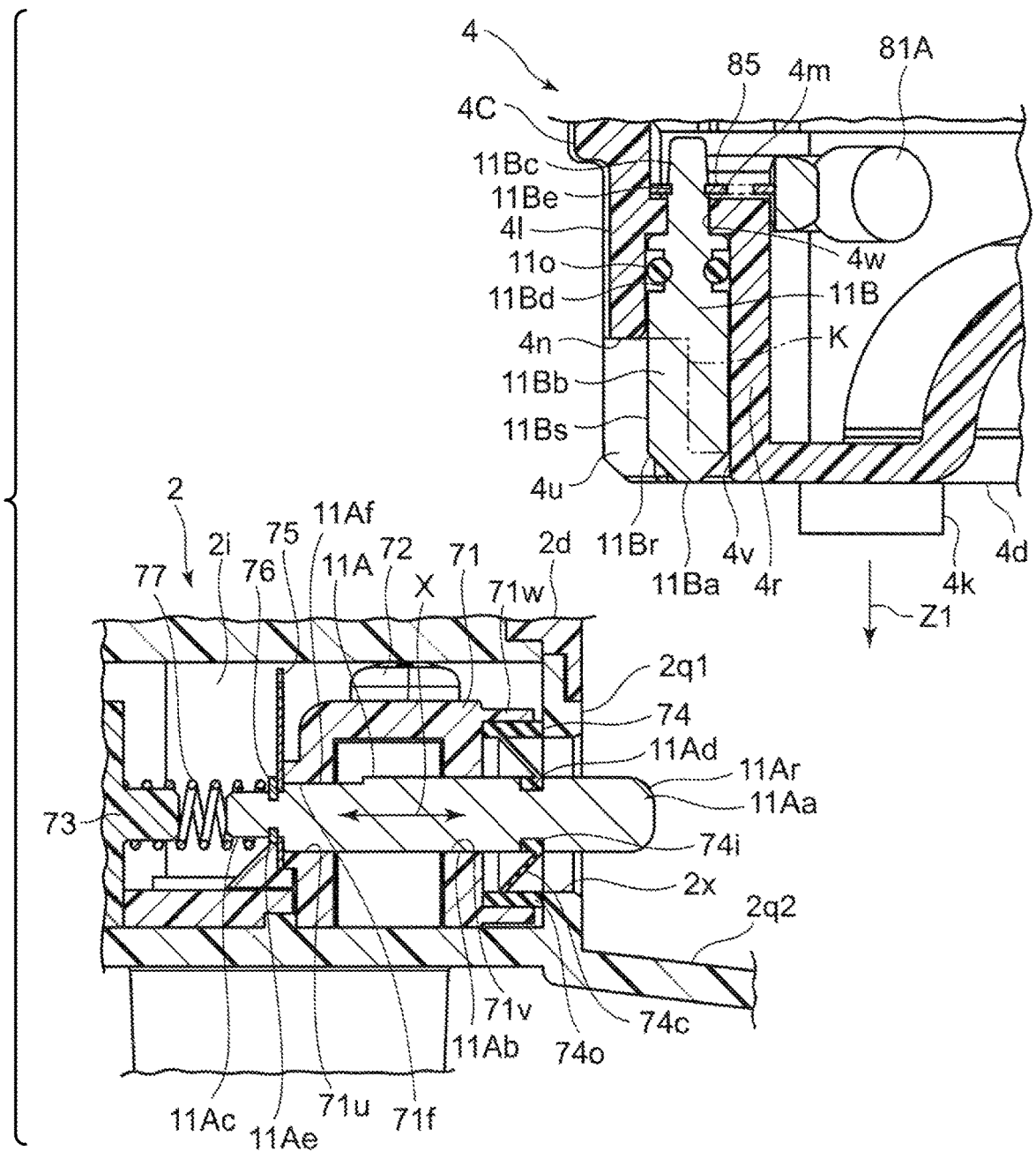
FIG. 11 is a cross-sectional view showing a configuration of the vicinity of a tank-side contact electrode on the bottom portion of the working tank and the vicinity of a main body-side contact electrode on a seating platform portion of the main body.

For example, the lower half of FIG. 11 shows a cross-sectional structure near the first main body-side contact electrode 11A of the seating platform portion 2d. With the seating platform portion 2d, a lateral hole 2x is formed through the side wall 2q1 of the recess 2q. A support member 71 for supporting the first main body-side contact electrode 11A is attached to the inner portion 2i of the seating platform portion 2d by a screw 72. The support member 71 conforms to the lateral hole 2x and has a cylindrical holder portion 71w and through holes 71u and 71v that have smaller diameters than the lateral hole 2x. The first main body-side contact electrode 11A is supported by being inserted in the through holes 71u and 71v so as to be able to slide in the lengthwise direction X.

The first main body-side contact electrode 11A includes a leading end 11Aa that protrudes from the lateral hole 2x of the side wall 2q1, a main portion 11Ab that is continuous with the leading end 11Aa and has an approximately constant outer diameter, and a small-diameter portion 11Ac that is continuous with the main portion 11Ab and has a diameter smaller than that of the main portion 11Ab.

Chamfering 11Ar, which serves as the second tapered surface that is tapered is carried out on the leading end 11Aa for convenience in coming into contact with the tank-side contact electrode 11B.

A ring-shaped groove 11Ad is formed around the portion of the main portion 11Ab that is near the lateral hole 2x. A cover member 74 made of rubber is provided between the holder portion 71w of the support member 71 and the ring-shaped groove 11Ad. The cover member 74 includes an outer circumferential cylindrical portion 74o that is held in the holder portion 71w (interposed between the support member 71 and the side wall 2q1), an inner circumferential cylindrical portion 74i that is attached by engaging with the ring-shaped groove 11Ad, and a cover surface 74c that joins the outer circumferential cylindrical portion 74o and the inner circumferential cylindrical portion 74i. The cover surface 74c is shaped like an inclined surface of a truncated cone. The cover member 74 covers the gap between the inner surface of the lateral hole 2x and the main body-side contact electrode 11A to prevent liquid such as the working liquid 4L, debris, dust, or the like from entering the interior portion 2i of the seating platform portion 2d. Even when the main body-side contact electrode 11A slides in the lengthwise direction X, the cover surface 74c bends, and therefore the function of protecting against liquid and dust is not impaired.

An E-ring-shaped wire member 75, a ring-shaped bush nut 76, and a coil spring 77 serving as an elastic member are fit into the small-diameter portion 11Ac. The E-ring-shaped wire member 75 is made of phosphor bronze (it is also possible to use stainless steel) and is press-fitted around the small-diameter portion 11Ac. The bush nut 76 is fit in the ring-shaped groove 11Ae formed around the portion of the small-diameter portion 11Ac that is adjacent to the wire member 75 in the lengthwise direction X. The bush nut 76 presses the wire member 75 such that the wire member 75 comes into contact with the main portion 11Ab, and fixes them such that they are connected. The coil spring 77 is provided compressed between another support member 73 provided facing the support member 71 and the bush nut 76. The first main body-side contact electrode 11A is biased by the coil spring 77 in an orientation in which the leading end 11Aa protrudes from the side wall 2q1 in the lengthwise direction X. When the working tank 4 (or the tank unit 3) is not mounted on the seating platform portion 2d, the wire member 75 comes into contact with the support member 71 and the protruding of the first main body-side contact electrode 11A is restricted.

A specific angular range in the circumferential direction, and in this example, the upper portion region 11Af, is formed flat on the portion of the main portion 11Ab that fits into the through hole 71u. In correspondence to this, a portion (in this example, an upper portion region) 71f of the inner circumference of an approximate circle is formed flat in the through hole 71u. According to these configurations, rotation about the central axis of the first main body-side contact electrode 11A is restricted with respect to the support member 71.

The other second, third, and fourth main body-side contact electrodes 12A, 13A, and 14A shown in FIG. 8 are configured similarly to the first main body-side contact electrode 11A. The first and second main body-side contact electrodes 11A and 12A and the third and fourth main body-side contact electrodes 13A and 14A are provided facing each other in the horizontal direction.

Note that in the unlikely event that the working liquid 4L or the like is spilled, a bottom wall 2q2 of the recess 2q inclines so as to gradually become lower toward the center, and a liquid discharge port 2o is provided in the center of the bottom wall 2q2.

Figure 9:
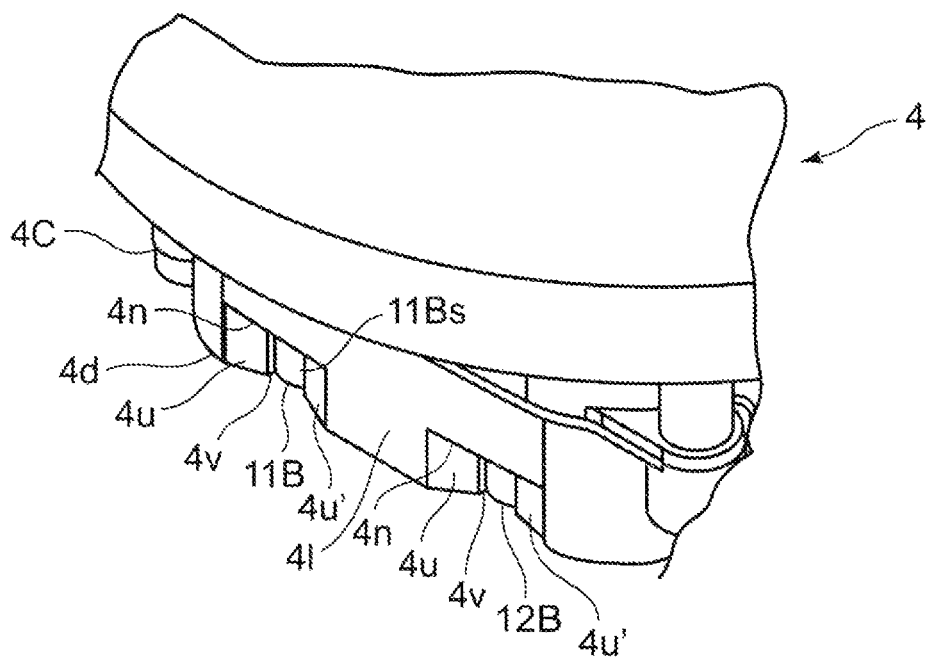
FIG. 9 is a diagram showing an enlarged view of the vicinity of a bottom portion of the working tank shown in FIG. 1.
Figure 10:
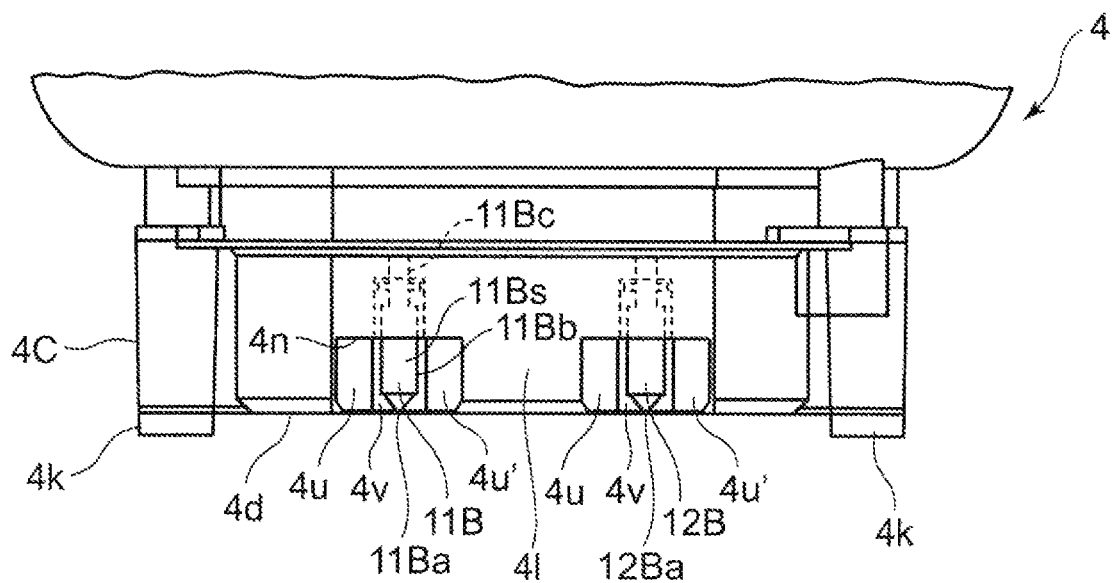
FIG. 10 is a diagram showing an enlarged view of the vicinity of the bottom portion of the working tank shown in FIG. 2.

FIGS. 9 and 10 show detailed enlarged views of the vicinity of the bottom portion of the working tank 4 shown in FIGS. 1 and 2 respectively. In this example, the first, second, third, and fourth tank-side contact electrodes 11B, 12B, 13B, and 14B are made of approximately circular rod-shaped titanium and are provided so as to penetrate through the outer wall (indicated by reference numeral 4l) of the bottom portion (third member 4C) of the working tank 4 as described above. Note that if the first, second, third, and fourth tank-side contact electrodes 11B, 12B, 13B, and 14B are approximately circular rod-shaped, the machining is easy in the manufacturing step.

In each of the first and second tank-side contact electrodes 11B and 12B, a hood portion 4n that extends in the left-right direction, a left and right pair of inclined surfaces 4u and 4u' that are located below the hood portion 4n and open toward the outside, and a cylindrical holding hole 4v that is continuous with the inclined surfaces 4u and 4u' and extends in the vertical direction through the inner side (underside) of the hood portion 4n are formed on the outer wall 4l. The same follows for the third and fourth tank-side contact electrodes 13B and 14B as well.

For example, the upper half of FIG. 11 shows a cross-sectional structure near the first tank-side contact electrode 11B on the bottom portion of the working tank 4. In the third member 4C, a circumferential wall portion 4r that forms a circumferential surface of the holding hole 4v and an end plate portion 4m that closes the upper portion of the holding hole 4v are formed on the inner side (underside) of the outer wall 4l. The holding hole 4v has an approximately constant inner diameter and reaches the end plate portion 4m through the inner side (underside) of the hood portion 4n from the outer bottom surface 4d.

The first tank-side contact electrode 11B is approximately circular rod-shaped, extends in the vertical direction along the outer wall 4l of the working tank 4, and is stored in the holding hole 4v. Specifically, the first tank-side contact electrode 11B has a lower end 11Ba that is exposed from the holding hole 4v, a main portion 11Bb that is continuous with the lower end 11Ba and has an approximately constant outer diameter, and a small-diameter portion 11Bc that is continuous above the main portion 11Bb and has a smaller diameter than the main portion 11Bb.

Chamfering 11Br, which serves as a first tapered surface that is tapered, is carried out on the lower end 11Ba for convenience in coming into contact with the main body-side contact electrode 11A.

The entire circumference of the outer circumferential surface of the upper portion (the upper half of the main portion 11Bb and the small-diameter portion 11Bc) of the first tank-side contact electrode 11B is embedded inside the outer wall 4l. The specific portion (portion that is leftward of or below the two-dot chain line K shown in FIG. 11) 11Bs that corresponds to a portion in the circumferential direction on the lower half of the main portion 11Bb is exposed from the outer wall. As a result, the remaining portion (the portion rightward of and above the two-dot chain line K shown in FIG. 11) other than the specific portion 11Bs in the circumferential direction of the main portion 11Bb is embedded inside of the outer wall 4l.

The ring-shaped groove 11Bd is formed around a specific location in the vertical direction on the upper half of the main portion 11Bb. An O ring 11o is fit into the ring-shaped groove 11Bd in order to provide a sealing property between the upper half of the main portion 11Bb and the circumferential surface of the holding hole 4v. Accordingly, even if the entirety of the working tank 4 is washed and/or disinfected, water or the disinfecting liquid can be prevented from entering the internal structure (in this example, the gap 4h in which the ultrasonic vibrator 10 is incorporated) of the working tank 4.

The small-diameter portion 11Bc extends above the end plate portion 4m through the through hole 4w formed in the end plate portion 4m. A ring-shaped groove 11Be that wraps around a portion of the small-diameter portion 11Bc located above the end plate portion 4m (accordingly, a portion located above the O ring 11o) is formed at that portion. An E-ring-shaped wire member 85 made of phosphor bronze (it is also possible to use stainless steel) is press-fitted around the ring-shaped groove 11Be. The wire member 85 locks the small-diameter portion 11Bc to the end plate portion 4m and prevents the first tank-side contact electrode 11B from falling downward out of the holding hole 4v. Also, the wire member 85 connects to the first tank-side contact electrode 11B, and along with the metal member 81A, forms a portion of the wire 81 that is connected to a first electrode 10p of the ultrasonic vibrator 10. Accordingly, the first tank-side contact electrode 11B and the first electrode 10p of the ultrasonic vibrator 10 can be favorably connected without soldering the first tank-side contact electrode 11B.

Thus, the first tank-side contact electrode 11B is firmly held by the wall of the working tank 4. The second, third, and fourth tank-side contact electrodes 12B, 13B, and 14B are configured similarly to the first tank-side contact electrode 11B.

The first, second, third, and fourth tank-side contact electrodes 11B, 12B, 13B, and 14B are made of titanium, and therefore even if the working tank 4 is immersed in a disinfecting liquid such as an aqueous solution of sodium hypochlorite, for example, an inconvenience such as rusting or corrosion of the exposed specific portions (e.g., 11Bs) of the first, second, third, and fourth tank-side contact electrodes 11B, 12B, 13B, and 14B does not occur.

The working tank 4 (or the tank unit 3; the same follows in this paragraph and the three paragraphs following this paragraph) is mounted on the seating platform portion 2d in the containing portion 2u of the main body 2 shown in FIG. 8 by being lowered from above in a standing orientation. At this time, the recesses 4q and 4q (see FIGS. 2 and 5) of the working tank 4 fit over the protrusions 2p and 2p on the inner surface of the containing portion 2u, and the working tank 4 is guided in a horizontal plane. Also, the orientation (direction) of the working tank 4 is set with respect to the main body 2 due to the approximately square tube-shaped bottom portion (third member 4C) of the working tank 4 being fit into the recess 2q of the seating platform portion 2d (note that the orientation of the working tank 4 with respect to the main body 2 is roughly set using the orientation of the handle 4t of the working tank 4). The first, second, third, and fourth main body-side contact electrodes 11A, 12A, 13A, and 14A come into contact with and connect to the first, second, third, and fourth tank-side contact electrodes 11B, 12B, 13B, and 14B of the working tank 4 respectively when the working tank 4 is lowered from above and seated.

Figure 12:
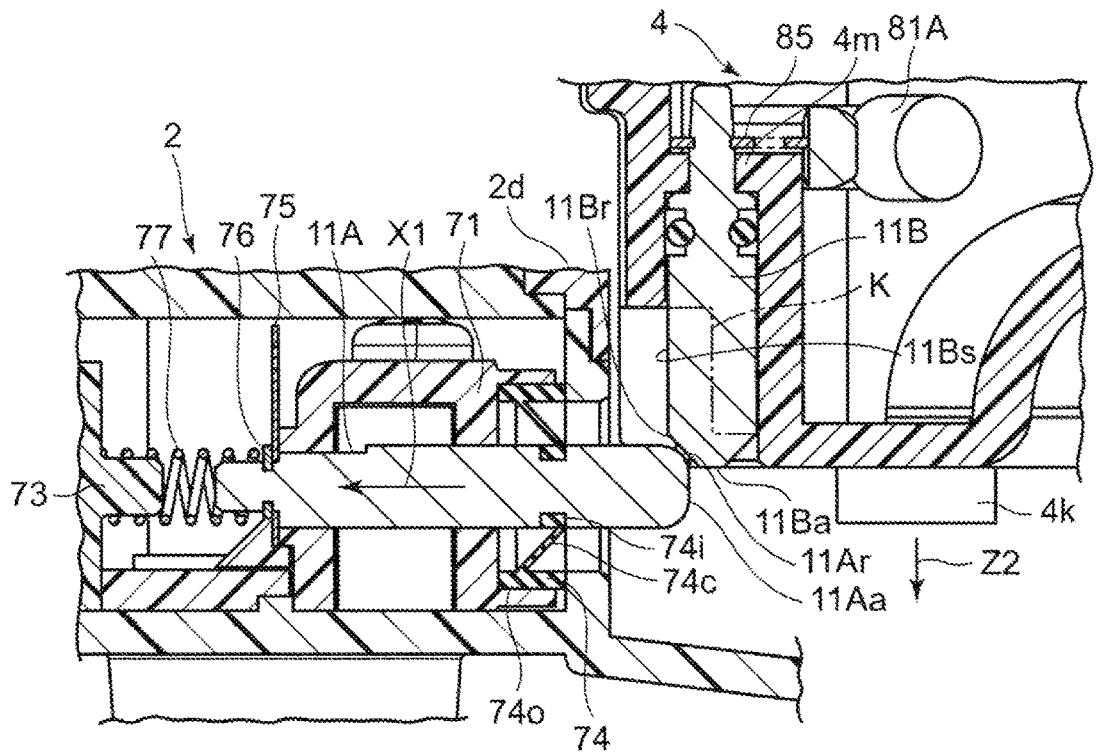
FIG. 12 is a diagram showing a process of mounting the working tank on the seating platform portion of the main body.
Figure 13:
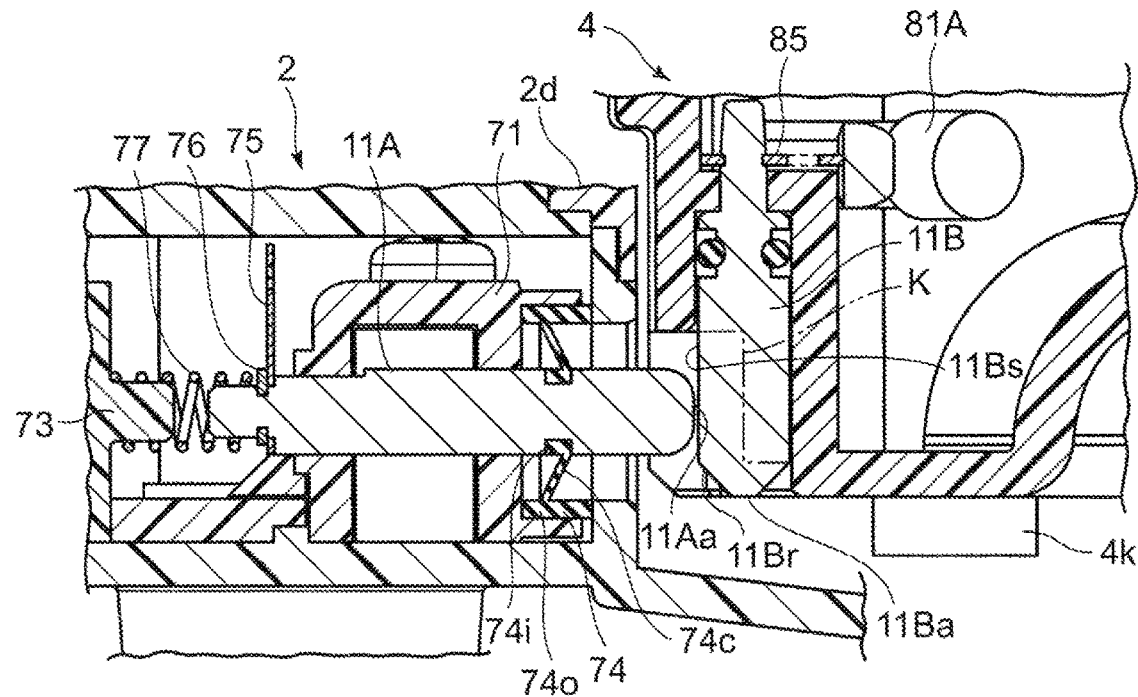
FIG. 13 is a diagram showing a state in which the working tank is mounted on the seating platform portion of the main body.

Specifically, i) When the working tank 4 is lowered onto the seating platform portion 2d of the main body 2 as indicated by the arrow Z1 in FIG. 11, the chamfering 11Br of the lower end 11Ba of the first tank-side contact electrode 11B comes into contact with the chamfering 11Ar of the leading end 11Aa of the first main body-side contact electrode 11A as shown in FIG. 12. Upon doing so, the first tank-side contact electrode 11B moves (retracts) in an orientation indicated by the arrow X1 in the lengthwise direction X against the biasing force of the coil spring 77. The same follows for the second, third, and fourth main body-side contact electrodes 12A, 13A, and 14A. Accordingly, even if the position of the working tank 4 is slightly misaligned in the horizontal plane, the lowering of the working tank 4 is allowed due to one of the main body-side contact electrodes retracting. In particular, in this example, the first and second main body-side contact electrodes 11A and 12A and the third and fourth main body-side contact electrodes 13A and 14A are provided facing each other in the horizontal direction on the side wall $2q1$ of the recess $2q$ of the seating platform portion 2d (see FIG. 8). Moreover, the chamfering 11Br is provided on the lower end 11Ba of the first tank-side contact electrode 11B, and the chamfering 11Ar is provided on the leading end 11Aa of the first main body-side contact electrode 11A. Accordingly, the degree of allowing positional misalignment in a horizontal plane of the working tank 4 is further increased.

ii) As indicated by the arrow Z2 in FIG. 12, when the working tank 4 is further lowered onto the seating platform portion 2d of the main body 2, as shown in FIG. 13, a state is entered in which the specific portion 11Bs of the outer circumferential surface of the first tank-side contact electrode 11B is in contact with the leading end 11Aa of the first main body-side contact electrode 11A. In this manner, the working tank 4 is smoothly mounted on the seating platform portion 2d of the main body 2. Also, even if debris or dust is attached to the specific portion 11Bs of the outer circumferential surface of the first tank-side contact electrode 11B, the debris and dust is wiped off due to sliding against the leading end 11Aa of the first main body-side contact electrode 11A when the specific portion 11Bs is lowered (wiping effect). Also, in the state in which the working tank 4 is mounted on the main body 2, the leading end 11Aa of the first main body-side contact electrode 11A is pressed to the specific portion 11Bs of the outer circumferential surface of the first tank-side contact electrode 11B due to the biasing force of the coil spring 77. Accordingly, a favorable connection is obtained between the first main body-side contact electrode 11A and the first tank-side contact electrode 11B. Also, in the state in which the working tank 4 is mounted on the main body 2, the first and second main body-side contact electrodes 11A and 12A and the third and fourth main body-side contact electrodes 13A and 14A, which are provided facing each other in the horizontal direction, press the working tank 4, and therefore the working tank 4 is positioned in the horizontal plane.

iii) Conversely, the working tank 4 is removed from the main body 2 by being pulled upward from the seating platform portion 2d of the main body 2.

Thus, with the ultrasonic nebulizer 1, the working tank 4 is configured to be detachable with respect to the main body 2. Also, as stated above, the medicine tank 6 and the medicine tank cover 7 are configured to be detachable with respect to the working tank 4 via the medicine tank support 5. Accordingly, the user (a doctor, a nurse, or the like) can easily take out only the working tank 4 by first removing the tank unit 3 (includes the working tank 4, the medicine tank support 5, the medicine tank 6, and the medicine tank cover 7) from the main body 2 in the tank unit mounted state, and then removing the medicine tank cover 7, the medicine tank 6, and the medicine tank support 5 in the stated order from the working tank 4 of the tank unit 3. Alternatively, it is possible to easily take out only the working tank 4 by first removing the medicine tank 6 and the medicine tank cover 7 from the medicine tank support 5 in the tank unit mounted state, then removing the medicine tank support 5 from the working tank 4, and furthermore removing the working tank 4 from the main body 2. Accordingly, the working tank 4 can be easily cleaned and/or disinfected separately. Also, the medicine tank cover 7, the medicine tank 6, and the medicine tank support 5 can each be easily cleaned and/or disinfected with a disinfecting liquid separately. Moreover, the first, second, third, and fourth tank-side contact electrodes 11B, 12B, 13B, and 14B are circular rod-shaped and extend in the vertical direction along the outer wall $4l$ of the working tank 4. Accordingly, if the working tank 4 is put in the upright orientation after the entirety of the working tank 4 is washed, no water remains on the specific portions (e.g., 11Bs) of the first, second, third, and fourth tank-side contact electrodes 11B, 12B, 13B, and 14B, which are exposed from the outer wall $4l$, and the water falls downward. As a result, it is possible to prevent an inconvenience such as rusting or corrosion of the first, second, third, and fourth tank-side contact electrodes 11B, 12B, 13B, and 14B due to accumulated water.

Also, as can be understood using FIG. 10, for example, the lower ends (e.g., 11Ba and 12Ba) of the first, second, third, and fourth tank-side contact electrodes 11B, 12B, 13B, and 14B are located above the lowest portions (i.e., the lower ends of the legs $4k$) of the working tank 4. Accordingly, even if the user places the working tank 4 on a platform that is wet with a liquid such as water or a disinfecting liquid, the lower ends of the first, second, third, and fourth tank-side contact electrodes 11B, 12B, 13B, and 14B do not get wet. Accordingly, it is possible to prevent a situation that causes short-circuiting between the first, second, third, and fourth tank-side contact electrodes 11B, 12B, 13B, and 14B or electrical leakage.

FIG. 9 schematically shows a schematic block configuration of the ultrasonic nebulizer 1 (which is in the tank unit mounted state). Note that in FIG. 9, for the sake of simplicity, the medicine tank support 5, the fourth main body-side contact electrode 14A, and the fourth tank-side contact electrode 14B are not shown.

The main body 2 (main portion 2b) is provided with the above-described power switch 48, an AC (alternating current) plug 49, the AC-DC conversion unit 20, a display substrate 50, a control circuit 51, an oscillation unit portion 34, a heat dissipation portion 35 and cooling fan 36 that are arranged along the oscillation unit portion 34, a current adjustment unit 37, the air cover detection unit 40, the medicine tank cover detection unit $4l$, and the working tank detection unit 42. In addition to the above-described operation switch portion 24, LED (light-emitting diode) display unit 25, and LCD (liquid crystal display element) display unit 26, the display substrate 50 is provided with a buzzer portion 27 and a CPU 28 that controls the overall operation of the ultrasonic nebulizer 1. The control substrate 51 is provided with a first DC-DC conversion unit 21, a second DC-DC conversion unit 22, a liquid shortage detection unit 29, an air-blowing motor control unit 30, an oscillation unit control unit 31, and a cooling fan lock detection unit 32.

The AC plug 49 is connected to a commercially-available AC power source (in this example, AC 100V). The power switch 48 is used to switch on and off the overall power of the ultrasonic nebulizer 1.

The AC-DC conversion unit 20 converts the AC 100V from the commercial AC power source into DC 48V. The DC 48V is used as a power source for causing the oscillation unit portion 34 and the ultrasonic vibrator 10 to operate.

The first DC-DC conversion unit 21 steps down the DC 48V to DC 12V. The DC 12V is used as a power source for causing the air cover detection unit 40, the air fan 38, and the cooling fan 36 to operate.

The second DC-DC conversion unit 22 steps down the DC 12V to DC 5V. The DC 5V is used mainly as system power to cause elements 24 to 28 on the display substrate 50 to operate.

As described above, the operation switch portion 24 is provided in order for a user (a doctor, a nurse, or the like) to perform switch input of an atomization amount, air flow, a timer, the start of spraying, and the like. The operation switch portion 24 transmits the switch input to the CPU 28.

Also, the LED display unit 25 and the LCD display unit 26 receive and display signals indicating the atomization amount, the air flow, the timer, the start of spraying, and states such as error from the CPU 28.

The buzzer portion 27 receives a signal indicating the end of a timer or a state such as error from the CPU 28 and performs notification using sound.

The liquid shortage detection unit 29 receives the voltage signal output from the liquid level sensor 15 in the tank unit mounted state and transmits a detection signal indicating whether or not the working liquid 4L in the working tank 4 has been filled to a necessary level to the CPU 28.

The air-blowing motor control unit 30 receives a PWM (pulse width modulation) signal for controlling the rotation rate of the air fan 38 from the CPU 28 and drives the air fan 38 according to the PWM signal.

In this example, the air fan 38 includes a sirocco fan, and a motor that rotates the sirocco fan at a rotation rate that corresponds to the PWM signal from the air-blowing motor control unit 30. The air fan 38 that is driven performs air-blowing 90 through the vent 2e to the tank unit 3 side.

The oscillation unit control unit 31 receives a PWM signal for controlling the atomization amount performed by the ultrasonic vibrator 10 from the CPU 28 and transmits it to the oscillation unit portion 34.

In this example, the oscillation unit portion 34 includes a Colpitts oscillation circuit, receives a PWM signal for driving the ultrasonic vibrator 10 from the oscillation unit control unit 31, generates an oscillation waveform (AC oscillation potential) based on the PWM signal, and outputs the oscillation waveform to the ultrasonic vibrator 10.

In this example, the heat dissipation portion 35 is composed of a metal plate (copper plate, etc.) that has fins. The heat dissipation portion 35 emits heat transmitted from the oscillation unit portion 34 to the outside of the main body 2 using wind from the cooling fan 36.

The current adjustment portion 37 adjusts the current that the oscillation unit portion 34 allows to flow to the ultrasonic vibrator 10.

The cooling fan lock detection unit 32 receives a voltage signal (this will be called a "cooling fan lock signal") that is generated when the cooling fan 36 stops (locks) and converts it to a voltage level that can be input to the CPU 28. The voltage-converted cooling fan lock signal is input to the CPU 28. If the cooling fan locks, the CPU 28 performs control for displaying an error stating that the cooling fan 36 has stopped on the LED display unit 25 and the LCD display unit 26 and stopping the spraying operation.

As stated above, the air cover detection unit 40 uses the magnetic force of the magnet 39 attached to the air cover 2c to detect whether or not the air cover 2c has been mounted on the main portion 2b. A detection result indicating whether or not the air cover 2c has been mounted is input to the CPU 28. If the air cover 2c has not been mounted, the CPU 28 performs control for displaying an error stating that the air cover 2c has not been mounted on the LED display unit 25 and the LCD display unit 26 and stopping the spraying operation.

Also, the medicine tank cover detection unit 4l uses the magnetic force of the magnet 17 incorporated in the medicine tank cover 7 to detect whether or not the medicine tank cover 7 has been correctly mounted with respect to the main portion 2b (whether or not the air duct 7a matches the vent 2e). A detection result indicating whether or not the medicine tank cover 7 has been correctly mounted is input to the CPU 28. If the medicine tank cover 7 has not been correctly mounted, the CPU 28 performs control for displaying an error stating that the medicine tank cover 7 has not been correctly mounted on the LED display unit 25 and the LCD display unit 26 and stopping the spraying operation.

In this example, the working tank detection unit 42 includes a hole IC, and detects whether or not the working tank 4 has been mounted on the seating platform portion 2d using the magnetic force of the magnet 16 incorporated in the working tank 4. A detection result indicating whether or not the working tank 4 has been mounted is input to the CPU 28. If the working tank 4 has not been mounted, the CPU 28 performs control for displaying an error stating that the working tank 4 has not been mounted on the LED display unit 25 and the LCD display unit 26 and stopping the spraying operation.

In the tank unit mounted state, as described above, the first and second main body-side contact electrodes 11A and 12A come into contact with and are connected to the first and second tank-side contact electrodes 11B and 12B, respectively. At the time of a spraying operation, the output from the oscillation unit portion 34 in the main body 2 is applied to the electrodes 10p and 10n of the ultrasonic vibrator 10 through the first and second main body-side contact electrodes 11A and 12A and the first and second tank-side contact electrodes 11B and 12B. Accordingly, the ultrasonic vibrator 10 in the working tank 4 is driven to generate ultrasonic vibration. The ultrasonic vibration is transmitted to the medicinal liquid 6L in the medicine tank 6 via the working liquid 4L, whereby the medicinal liquid 6L in the medicine tank 6 is atomized. The atomized medicinal liquid (aerosol) 91 is blown by the air-blowing 90 from the air fan 38, and in this example, is supplied to the patient through the suction hose 8 and the mouthpiece 9. Note that instead of the mouthpiece 9, it is possible to include an inhalation mask, a glass nasal olive for inhaling through the nostrils, or the like.

The above-described embodiment is merely an example and can be modified in various ways without departing from the scope of the invention. The various characteristics of the above-described embodiment can be realized independently, but it is also possible to combine the characteristics.

REFERENCE SIGNS LIST

1 Ultrasonic nebulizer
2 Main body
2u Containing portion
3 Tank unit

4 Working tank
5 Medicine tank support
6 Medicine tank
7 Medicine tank cover
10 Ultrasonic vibrator

The invention claimed is:

1. An ultrasonic nebulizer comprising:
a working tank in which an ultrasonic vibrator is incorporated and in which a working liquid is stored facing the ultrasonic vibrator;
a medicine tank that stores a medicinal liquid, at least a bottom portion of the medicine tank being dipped in the working liquid; and
a main body that includes (i) a containing portion for surrounding and containing the working tank, (ii) an oscillation circuit that is configured to drive the ultrasonic vibrator, and (iii) main body-side contact electrodes that are configured to emit an output of the oscillation circuit, wherein:
the medicine tank is configured to be detachable with respect to the working tank,
the working tank is configured to be detachable with respect to the main body,
the working tank includes rod-shaped tank-side contact electrodes that extend in a vertical direction along an outer wall of the working tank, specific portions corresponding to portions in a circumferential direction of outer circumferential surfaces of the tank-side contact electrodes are exposed from the outer wall, and the remaining portions other than the specific portions in the circumferential direction of the outer circumferential surfaces of the tank-side contact electrodes are embedded inside of the outer wall and are connected to electrodes of the ultrasonic vibrator,
when the working tank is mounted on the main body, the main body-side contact electrodes come into contact with the specific portions of the outer circumferential surfaces of the tank-side contact electrodes, and
the main body-side contact electrodes (i) have elongated rod shapes, (ii) are configured to slide in a lengthwise direction in lateral holes penetrating through a side wall of the containing portion, and (iii) are biased by elastic members, in an orientation in which leading ends of the main body-side contact electrodes are exposed from the side wall in the lengthwise direction.

2. The ultrasonic nebulizer according to claim 1, wherein:
the tank-side contact electrodes are provided at portions on mutually opposite sides of the outer wall of the working tank, and
the main body-side contact electrodes are provided facing each other in a horizontal direction on the side wall of the containing portion.

3. The ultrasonic nebulizer according to claim 1, wherein the tank-side contact electrodes have circular rod shapes.

4. The ultrasonic nebulizer according to claim 3, wherein:
first tapered surfaces that are tapered are provided on lower ends of the tank-side contact electrodes, and
second tapered surfaces that are tapered are provided on the leading ends of the main body-side contact electrodes.

5. The ultrasonic nebulizer according to claim 4, wherein:
the entire circumference of the outer circumferential surface of an upper portion of each tank-side contact electrode is embedded inside the outer wall, and
O rings are fit into the upper portions of the tank-side contact electrodes so as to provide a sealing property between the upper portions of the tank-side contact electrodes and a wall of the working tank that surrounds the upper portions.

6. The ultrasonic nebulizer according to claim 5, wherein:
ring-shaped grooves are formed around portions the upper portions of the tank-side contact electrodes that are above the O rings, and
the tank-side contact electrodes are connected to the electrodes of the ultrasonic vibrator via E rings that are press-fit into the ring-shaped grooves.

7. The ultrasonic nebulizer according to claim 1, wherein lower ends of the tank-side contact electrodes are located above the lowest portions of the working tank.

8. The ultrasonic nebulizer according to claim 1, wherein the tank-side contact electrodes are made of titanium.

* * * * *